United States Patent
Imamura

(10) Patent No.: US 9,967,962 B2
(45) Date of Patent: May 8, 2018

(54) ELECTRONIC RADIOGRAPHY SYSTEM AND SIGNAL RELAY DEVICE

(71) Applicant: FUJIFILM Corporation, Tokyo (JP)

(72) Inventor: Ryou Imamura, Ashigarakami (JP)

(73) Assignee: FUJIFILM Corporation, Tokyo (JP)

( * ) Notice: Subject to any disclaimer, the term of this patent is extended or adjusted under 35 U.S.C. 154(b) by 543 days.

(21) Appl. No.: 14/608,485

(22) Filed: Jan. 29, 2015

(65) Prior Publication Data

US 2015/0164461 A1 Jun. 18, 2015

Related U.S. Application Data

(63) Continuation of application No. PCT/JP2013/069476, filed on Jul. 18, 2013.

(30) Foreign Application Priority Data

Aug. 22, 2012 (JP) ................................ 2012-183094
May 23, 2013 (JP) ................................ 2013-109302

(51) Int. Cl.
H05G 1/44 (2006.01)
H05G 1/42 (2006.01)
(Continued)

(52) U.S. Cl.
CPC .............. *H05G 1/44* (2013.01); *A61B 6/542* (2013.01); *G01T 1/026* (2013.01); *G01T 1/1603* (2013.01);
(Continued)

(58) Field of Classification Search
CPC .. A61B 6/00; A61B 6/54; A61B 6/542; A61B 6/56; A61B 6/563; A61B 6/566;
(Continued)

(56) References Cited

U.S. PATENT DOCUMENTS 8,841,620 B2 9/2014 Okada
2013/0077744 A1* 3/2013 Kamiya ............... A61B 6/5241
378/62
(Continued)

FOREIGN PATENT DOCUMENTS

JP 2011-502699 A 1/2011
JP 2011-174908 A 9/2011
(Continued)

OTHER PUBLICATIONS

International Search Report, issued in PCT/JP2013/069476, dated Aug. 13, 2013.
(Continued)

*Primary Examiner* — Anastasia Midkiff
(74) *Attorney, Agent, or Firm* — Birch, Stewart, Kolasch & Birch, LLP

(57) ABSTRACT

A signal relay device comprises a first connection I/F, to which an emission switch is connected, a second connection I/F, to which an emission signal I/F of an electronic cassette is connected, and a third connection I/F, to which a switch I/F of a source control device is connected, and a signal processing unit. The signal processing unit generates an emission execution signal during a time period in which an emission command signal from the emission switch and an emission enable signal from the electronic cassette are inputted. The source control device drives an X-ray tube to allow X-ray emission while the emission execution signal is inputted.

17 Claims, 9 Drawing Sheets

(51) Int. Cl.
| | |
|---|---|
| *H05G 1/40* | (2006.01) |
| *H05G 1/38* | (2006.01) |
| *G01T 1/02* | (2006.01) |
| *A61B 6/00* | (2006.01) |
| *G05B 23/02* | (2006.01) |
| *H05G 1/56* | (2006.01) |
| *G01T 1/16* | (2006.01) |
| *G05B 19/042* | (2006.01) |
| *G05B 1/03* | (2006.01) |
| *G05B 13/04* | (2006.01) |
| *G05B 11/06* | (2006.01) |
| *G05B 19/414* | (2006.01) |
| *G05B 19/10* | (2006.01) |
| *H04N 5/32* | (2006.01) |

(52) U.S. Cl.
CPC .......... *G05B 23/0286* (2013.01); *H05G 1/38* (2013.01); *H05G 1/40* (2013.01); *H05G 1/42* (2013.01); *H05G 1/56* (2013.01); *A61B 6/4233* (2013.01); *A61B 6/4283* (2013.01); *A61B 6/54* (2013.01); *A61B 6/566* (2013.01); *G05B 1/03* (2013.01); *G05B 11/06* (2013.01); *G05B 13/041* (2013.01); *G05B 19/0423* (2013.01); *G05B 19/0425* (2013.01); *G05B 19/106* (2013.01); *G05B 19/414* (2013.01); *H04N 5/32* (2013.01)

(58) Field of Classification Search
CPC .. G01T 1/00; G01T 1/02; G01T 1/026; G01T 1/16; G01T 1/1603; G01T 1/161; G01T 1/17; G01T 1/175; G01T 1/2015; G01T 1/24; H01J 7/44; H01J 23/00; H01J 23/16; H01J 23/34; H01J 35/00; H01J 35/02; H01J 35/025; H01J 37/00; H01J 37/02; H01J 37/04; H01J 37/24; H01J 37/241; H01J 37/242; H01J 37/243; H01J 37/244; H01J 37/248; H01J 99/00; H01J 2235/00; H01J 2235/02; H01J 2235/023; H01J 2237/00; H01J 2237/04; H01J 2237/06; H01J 2237/24592; H01J 2237/248; H01J 2237/2485; H01J 2237/2487; H02J 13/00; H02J 13/0006; H02J 13/0013; H02J 13/0079; H02J 13/0082; H02M 1/00; H02M 11/00; H02M 2001/0003; H02M 2001/0012; G05B 1/00; G05B 1/01; G05B 1/03; G05B 11/00; G05B 11/01; G05B 11/06; G05B 11/14; G05B 11/16; G05B 11/26; G05B 11/32; G05B 13/00; G05B 13/02; G05B 13/04; G05B 13/041; G05B 13/042; G05B 13/044; G05B 13/045; G05B 13/047; G05B 13/048; G05B 15/00; G05B 15/02; G05B 17/00; G05B 17/02; G05B 19/00; G05B 19/02; G05B 19/04; G05B 19/041; G05B 19/042; G05B 19/0421; G05B 19/0423; G05B 19/0425; G05B 19/048; G05B 19/10; G05B 19/106; G05B 19/404; G05B 19/414; G05B 21/00; G05B 21/02; G05B 23/00; G05B 23/02; G05B 23/0205; G05B 23/0259; G05B 23/0286; G05B 2219/00; G05B 2219/10; G05B 2219/11; G05B 2219/1103; G05B 2219/1108; G05B 2219/1158; G05B 2219/1167; G05B 2219/14117; G05B 2219/15097; G06F 1/26; H05G 1/38; H05G 1/40; H05G 1/42; H05G 1/44; H05G 1/56

See application file for complete search history.

(56) References Cited

U.S. PATENT DOCUMENTS

| | | | |
|---|---|---|---|
| 2013/0121464 A1* | 5/2013 | Tajima | A61B 6/542 378/62 |
| 2014/0072103 A1* | 3/2014 | Kitano | A61B 6/4233 378/62 |
| 2014/0177798 A1* | 6/2014 | Kitagawa | A61B 6/4233 378/62 |

FOREIGN PATENT DOCUMENTS

| | | | | |
|---|---|---|---|---|
| WO | WO 2009/067189 A1 | 5/2009 | | |
| WO | WO 2013042676 A1 * | 3/2013 | ........... | A61B 6/4233 |

OTHER PUBLICATIONS

Written Opinion of the International Searching Authority, issued in PCT/JP2013/069476, dated Aug. 13, 2013.

\* cited by examiner

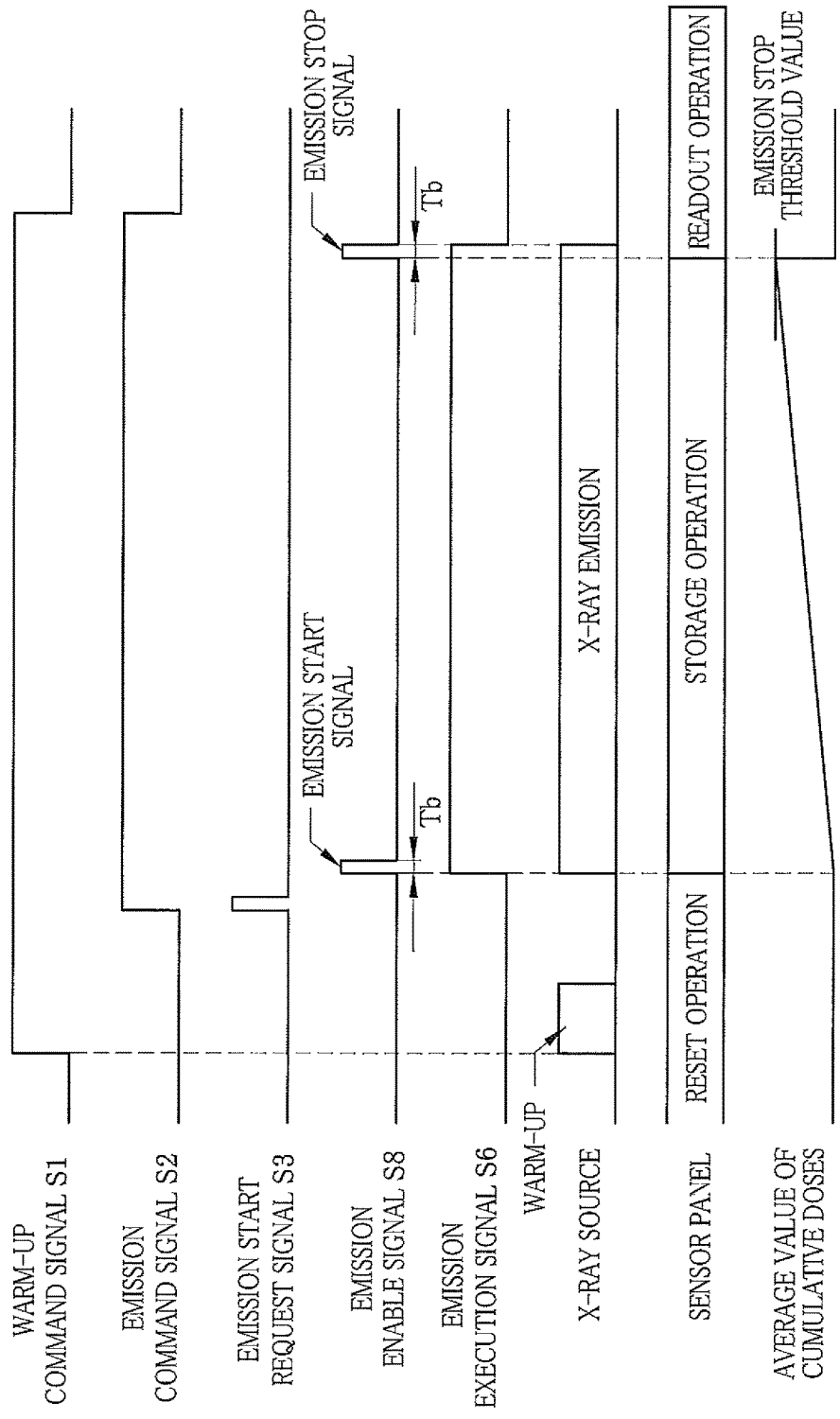

ELECTRONIC RADIOGRAPHY SYSTEM AND SIGNAL RELAY DEVICE

CROSS-REFERENCE TO RELATED APPLICATIONS

This application is a Continuation of PCT International Application No. PCT/JP2013/069476 filed on Jul. 18, 2013, which claims priority under 35 U.S.C. § 119(a) to Japanese Patent Application No. 2012-183094, filed Aug. 22, 2012 and Japanese Patent Application No. 2013-109302, filed May 23, 2013. Each of the above applications is hereby expressly incorporated by reference, in its entirety, into the present application.

BACKGROUND OF THE INVENTION

1. Field of the invention

The present invention relates to an electronic radiography system for imaging radiographic images and a signal relay device.

2. Description Related to the Prior Art

In medical fields, radiography systems, for example, X-ray imaging systems using X-rays are widely used to examine inside human bodies. The X-ray imaging system comprises an X-ray generating apparatus that generates X-rays and an X-ray imaging apparatus for imaging X-ray images generated by the X-rays passed through a subject (patient). The X-ray generating apparatus comprises an X-ray source that applies the X-rays to the subject, a source control device that controls the drive of the X-ray source, and an emission switch that allows emission of the X-rays.

X-ray image detection devices (hereinafter referred to as the electronic X-ray image detection devices) that electronically detect X-ray images have been prevailing as X-ray imaging apparatuses, in place of X-ray image recording devices using X-ray films and X-ray image detection devices using IP plates. In the X-ray imaging system (hereinafter referred to as the electronic X-ray imaging system) using the electronic X-ray image detection device, the electronic X-ray image detection device is connected to a console. The X-ray image detected by the electronic X-ray image detection device is transmitted to the console, and displayed on a display of the console. The electronic X-ray image detection device comprises a sensor panel referred to as a flat panel detector (FPD). The sensor panel has an imaging field in which pixels are arranged in a matrix. Each pixel stores a signal charge in accordance with an amount of incident X-rays. The sensor panel stores signal charge in each pixel at the time of X-ray imaging, and the stored signal charges are read out to a signal processing circuit through switching elements such as TFTs (thin film transistors). The signal processing circuit converts the signal charges into a voltage signal and outputs the voltage signal as an X-ray image signal.

Recently, there has been a growing trend to modify a conventional or existing X-ray imaging system, which uses the X-ray image recording device using the X-ray film or the X-ray image detection device using the IP plate, into the electronic X-ray imaging system. In this modification, the electronic X-ray detection device and the console are replaced while the existing X-ray generating apparatus is used without replacement because the modifications to the entire system results in high introduction cost.

The electronic X-ray image detection device differs from the X-ray image recording device using the X-ray film and the X-ray image detection device using the IP plate in that a reset operation, in which dark charge noise is discharged, needs to be performed at regular time intervals before imaging. When the X-ray imaging is started, a storage operation to store a signal charge, which corresponds to the amount of the incident X-rays, in each pixel is started after the reset operation. Therefore it is necessary to synchronize the timing for starting the storage operation with the timing to start the X-ray emission from the X-ray source. In a case where the existing X-ray generating apparatus is used for the electronic X-ray imaging system, it is necessary to make modifications so as to transmit an emission command signal from the emission switch to each of the source control device and the electronic X-ray image detection device.

In PCT International Publication No. WO 2009/067189 (corresponding to Japanese translation of PCT international application publication No. 2011-502699), a signal relay device (which serves as both connection circuit and control circuit) is used to make minimum modifications to the existing X-ray generating apparatus. The signal relay device is connected to each of the emission switch (operation switch), the source control device (console and X-ray generator), and the electronic X-ray image detection device (DR receiver panel). The signal relay device transmits the emission command signal (exposure signal) from the emission switch to each of the source control device and the electronic X-ray image detection device.

An electronic X-ray imaging system described in the PCT International Publication No. WO 2009/067189 is provided with an automatic exposure control device (hereinafter abbreviated as the AEC device) to control exposure of the X-ray image. The AEC device stops the X-ray emission from the X-ray source when an X-ray dose (cumulative dose) reaches a target amount. In a case where the AEC device is used, it is necessary to input an emission stop signal from the AEC device to the source control device. For this reason, the source control device is provided with an AEC I/F, which receives the emission stop signal from the AEC device, in addition to a switch I/F, to which the emission command signal is inputted. The source control device drives the X-ray source to allow the X-ray emission while the emission command signal is inputted from the switch I/F, but disables the X-ray source to forcefully terminate its X-ray emission upon the input of the emission stop signal from the AEC device through the AEC I/F.

The electronic X-ray image detection device described in U.S. Pat. No. 8,841,620 (corresponding to Japanese Patent Laid-Open Publication No. 2011-174908) comprises an AEC function to measure the X-ray dose with a sensor panel and determine timing to stop the X-ray emission from the X-ray source.

In many cases, the AEC I/F of the source control device allows connecting a predetermined AEC device only. In a case where the AEC function of the electronic X-ray image detection device of the U.S. Pat. No. 8,841,620 is utilized for the X-ray generating apparatus of the PCT International Publication No. WO 2009/067189, it is necessary to modify the AEC I/F of the source control device in accordance with the specifications of the AEC function of the electronic X-ray image detection device. It is also necessary to modify a control sequence for the source control device to stop the X-ray emission. Even if the source control device does not have the AEC I/F, it is necessary to modify the source control device to utilize the AEC function of the electronic X-ray image detection device.

SUMMARY OF THE INVENTION

An object of the present invention is to provide an electronic radiography system and a signal relay device, capable of using an AEC function of an electronic radiographic image detection device without modifying a source control device.

In order to achieve the above and other objects, the electronic radiography system according to the present invention comprises a radiation generating apparatus, an electronic radiographic image detection device, and a signal relay device. The radiation generating apparatus comprises a radiation source, an emission switch, and a source control device. The radiation source emits radiation to a subject. The emission switch generates an emission command signal to command start of emission of the radiation. The source control device has a switch I/F to which the emission command signal is inputted. The source control device allows the radiation source to emit the radiation for radiography while the emission command signal is inputted.

The electronic radiographic image detection device comprises a sensor panel, a dose measurement sensor, and a controller. The sensor panel converts the radiation passed through the subject into an electric signal during the radiography and outputs a radiographic image of the subject. The dose measurement sensor measures a dose of the radiation during the radiography. The controller generates an emission enable signal that determines a time period from a time when the emission is enabled in response to the emission command signal until a time for stopping the emission. The time for stopping the emission is determined by the controller through determining that a radiation exposure dose of the subject has reached a predetermined value based on measurement with the dose measurement sensor.

The signal relay device comprises a first connection I/F, a second connection I/F, a signal processing unit, and a third connection I/F. The first connection I/F receives the emission command signal from the emission switch. The second connection I/F transmits the emission command signal to the electronic radiographic image detection device and receives the emission enable signal from the electronic radiographic image detection device. The signal processing unit generates an emission execution signal based on the emission command signal and the emission enable signal. The third connection I/F transmits the emission execution signal to the switch I/F of the source control device.

It is preferred that normal pixels, which detect the radiographic image, and measurement pixels, being the dose measurement sensor, are placed in a mixed arrangement in two-dimensions in the sensor panel.

It is preferred that an electronic cassette is used as the electronic radiographic image detection device. The electronic cassette comprises the sensor panel and the controller, which are accommodated in a portable housing.

It is preferred that the emission command signal is outputted continuously while the emission switch is operated.

It is preferred that the signal processing unit is configured to perform first to four steps. In the first step, the signal processing unit transmits an emission start request signal to the electronic radiographic image detection device through the second connection I/F in response to input of the emission command signal. The emission start request signal asks whether to start the emission of the radiation. In the second step, the signal processing unit receives the emission enable signal from the electronic radiographic image detection device through the second connection I/F. In the third step, the signal processing unit generates an ON signal in response to the emission enable signal, from the time when the emission is enabled until the time for stopping the emission. In the fourth step, the signal processing unit generates the emission execution signal based on the emission command signal and the ON signal.

It is preferred that the signal processing unit comprises a synchronization processing unit for performing the first to third steps and an AND circuit for performing the fourth step.

It is preferred that the emission enable signal has a waveform outputted continuously from the time when the emission is enabled until the time for stopping the emission.

It is preferred that the emission enable signal has a pulse waveform and is generated repeatedly at predetermined intervals from the time when the emission is enabled until the time for stopping the emission.

It is preferred that the emission enable signal has a pulse-like emission start signal generated at the time when the emission is enabled and a pulse-like emission stop signal generated at the time for stopping the emission.

It is preferred that the signal relay device has a conversion mode, which is chosen in a case where the electronic radiographic image detection device is used, and a through mode, which is chosen in a case where the electronic radiographic image detection device is not used. In the conversion mode, the signal processing unit is activated and the emission execution signal is generated. In the through mode, the emission command signal inputted from the emission switch through the first connection I/F is inputted as the emission execution signal to the source control device through the third connection I/F. In the through mode, a radiographic image recording device using a radiation film or a radiographic image detection device using an IP plate is used.

It is preferred that the emission switch generates a warm-up command signal, which commands warm-up of the radiation source, before outputting the emission command signal. The signal relay device outputs the warm-up command signal to the source control device through the third connection I/F.

The signal relay device according to the present invention is used in an electronic radiography system comprising a radiation generating apparatus and an electronic radiographic image detection device. The signal relay device comprises a first connection I/F, a second connection I/F, and a third connection I/F.

The radiation generating apparatus comprises a radiation source, an emission switch, and a source control device. The radiation source emits radiation to a subject. The emission switch generates an emission command signal to command start of emission of the radiation. The source control device allows the radiation source to emit the radiation for radiography while the emission command signal is inputted.

The electronic radiographic image detection device detects a radiographic image of the subject. The electronic radiographic image detection device generates an emission enable signal, which determines a time period from a time when emission of the radiation is enabled in response to the emission command signal until a time for stopping the emission. The time for stopping the emission is determined by determining that a radiation exposure dose of the subject has reached a predetermined value based on measurement with the dose measurement sensor.

The first connection I/F receives the emission command signal from an emission switch. The second connection I/F transmits the emission command signal to the electronic radiographic image detection device and receives the emission enable signal from the electronic radiographic image detection device. The signal processing unit generates the emission execution signal based on the emission command signal and the emission enable signal. The third connection I/F transmits the emission execution signal to the source control device to allow the emission of the radiation.

According to the present invention, the signal relay device transmits the emission command signal from the emission switch to the electronic radiographic image detection device, and synchronizes the radiation generating apparatus with the electronic radiographic image detection device, and receives the emission enable signal, which represents a time period from the time when the emission is enabled in response to the emission command signal until the time for stopping the emission determined by the AEC function, from the electronic radiographic image detection device, and generates the emission execution signal based on the emission enable signal and the emission command signal. The source control device allows the radiation source to emit the radiation while the emission execution signal is inputted to the source control device. The emission execution signal generated by the signal relay device is inputted to the source control device in place of the conventional emission command signal. Thus, according to the present invention, the AEC function of the electronic radiographic image detection device is utilized without modifying the source control device.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein:

FIG. 9 is a timing chart for the X-ray imaging using an emission start signal and an emission stop signal.

DESCRIPTION OF THE PREFERRED EMBODIMENTS

Figure 1:
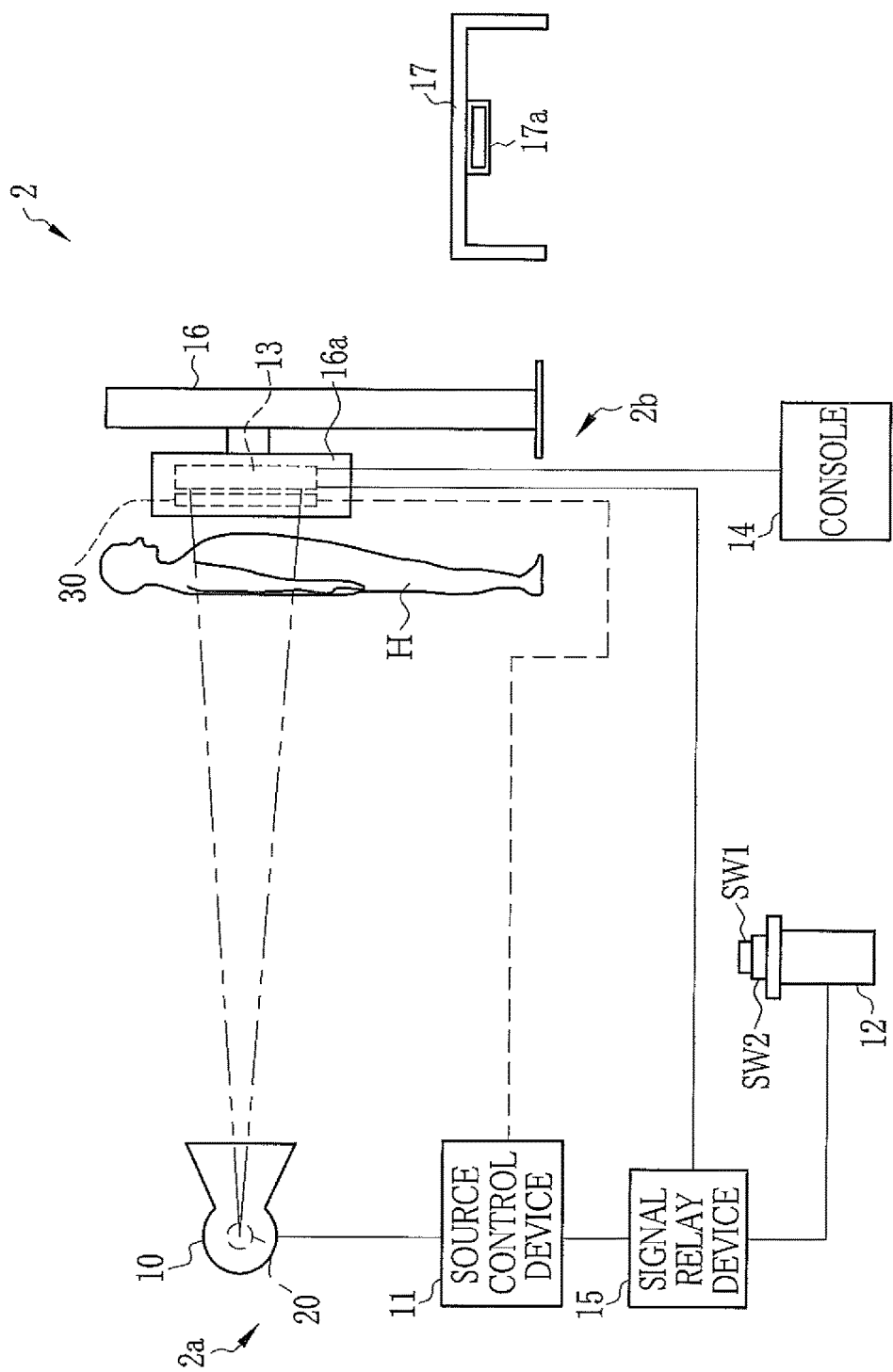
FIG. 1 is a schematic view of an electronic X-ray imaging system after modification or retrofit.
Figure 2:
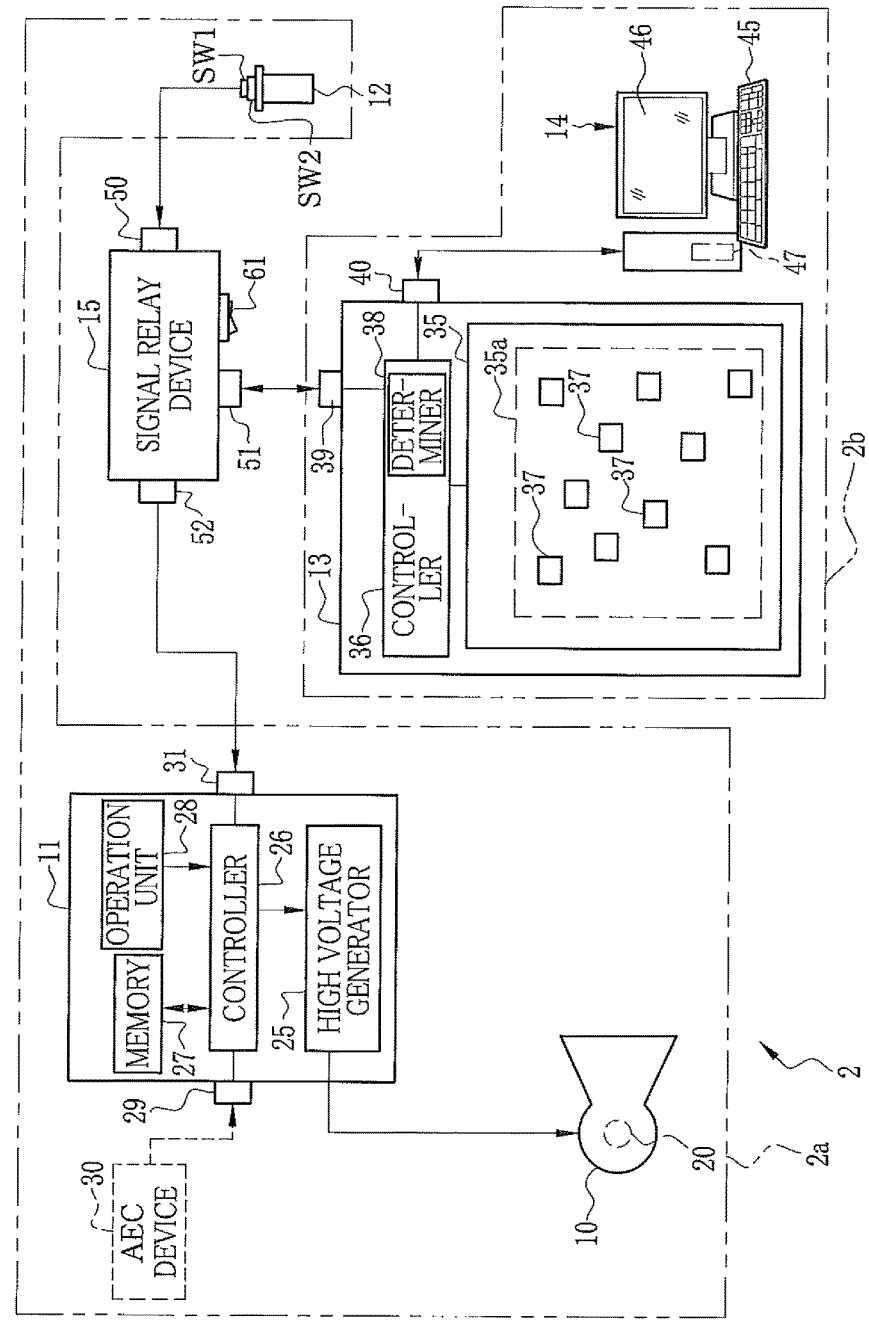
FIG. 2 is a block diagram of the electronic X-ray imaging system after the modification.

In FIGS. 1 and 2, an electronic X-ray imaging system 2 is produced by retrofitting or making modifications to an existing or conventional X-ray imaging system. The existing X-ray imaging system comprises an X-ray generating apparatus 2a, an imaging stand 16 that allows imaging of a patient H in a standing position, and an imaging table 17 that allows imaging of a patient H in a lying position. The X-ray generating apparatus 2a comprises an X-ray source 10 that generates X-rays, a source control device 11 that controls operation of the X-ray source 10, and an emission switch 12 that commands the X-ray source 10 to start warm-up and to start emission of the X-rays. The X-ray source 10 is moved along a ceiling or the like by a source moving device (not shown), to be compatible for use by the imaging stand 16 and the imaging table 17. In the existing X-ray imaging system, a film cassette using an X-ray film or an IP cassette 80 (see FIG. 3) using an IP plate is inserted into a holder 16a of the imaging stand 16 or a holder 17a of the imaging table 17.

An X-ray imaging apparatus 2b and a signal relay device 15 are necessary to convert the existing X-ray imaging system into the state-of-the-art electronic X-ray imaging system 2. The X-ray imaging apparatus 2b is a portable X-ray image detection device comprising an electronic cassette 13 and a console 14. The electronic cassette 13 detects the X-rays passed through a subject (patient) H and outputs an X-ray image. The console 14 controls operation of the electric cassette 13 and performs display processing of an X-ray image. The electronic cassette 13 is used as an electronic X-ray image detection device having an AEC (Automatic Exposure Control) function. The signal relay device 15 allows the use of the existing X-ray generating apparatus 2a with the electronic cassette 13 having the AEC function. The signal relay device 15 relays signals transmitted among the emission switch 12, the source control device 11, and the electronic cassette 13.

The X-ray source 10 comprises an X-ray tube 20 and an irradiation field limiter (collimator, not shown) that limits an irradiation field of the X-rays from the X-ray tube 20. The X-ray tube 20 has a cathode, being a filament that releases thermions, and an anode (target). The thermions hit the target and thereby the X-rays are emitted. The irradiation field limiter may be composed of, for example, four lead plates that block the X-rays. The four lead plates are arranged in the shape of a rectangle to form a maximum irradiation opening. To limit the irradiation field, the size of the irradiation opening is changed by moving the lead plates.

The source control device 11 comprises a high-voltage generator 25 that boosts input voltage and a controller 26 that controls the high-voltage generator 25 such that tube voltage and tube current are properly supplied to the X-ray source 10. The high-voltage generator 25 is connected to the X-ray source 10 through a high voltage cable. The tube voltage determines radiation quality (energy spectrum) of the X-rays emitted from the X-ray source 10. The tube current determines an X-ray dose (or simply referred to as the dose) per unit time.

A memory 27 stores in advance several types of imaging conditions (e.g. the tube voltage, the tube current, and the irradiation time). An operator (e.g. a radiological technologist or the like) manually sets the imaging conditions through an operation unit 28 composed of a touch panel or the like. The irradiation time is set to avoid an excess dose that adversely affects the subject H. The irradiation time is set to achieve a dose slightly greater than that achieved by the AEC. For example, the maximum irradiation time, which is set for each body part to be imaged in view of safety, is used. Normally, the AEC terminates the X-ray emission before it reaches the maximum irradiation time.

While an emission execution signal from the signal relay device 15 is inputted to the controller 26 through a switch I/F 31, the controller 26 drives the high-voltage generator 25 to allow the X-ray source 10 to emit the X-rays. Upon input of an emission stop signal from an AEC I/F 29, the controller 26 stops the X-ray emission from the X-ray source 10 even during the input of the emission execution signal. The controller 26 incorporates a countdown timer (not shown) that counts the irradiation time, and forcefully terminates the X-ray emission when the count (irradiation time) reaches the irradiation time (time limit) set in the memory.

In the existing X-ray imaging system that uses the film cassette or the IP cassette 80, an AEC device 30 is connected to the AEC I/F 29, as shown by dotted lines in FIGS. 1 and 2. The AEC device 30 is composed of an ion chamber, for example. The AEC device 30 is disposed on the front or the back of the cassette inserted into the holder 16a or 17a of the imaging stand 16 or the imaging table 17. In FIG. 1, the AEC device 30 is attached to the holder 16a of the imaging stand 16 by way of example. In the electronic X-ray imaging system after the modifications or retrofit, the AEC device 30 is unnecessary, so that the AEC device 30 is disconnected from the AEC I/F 29 and removed from the imaging stand 16.

The operator operates the emission switch 12 to start the X-ray emission. The emission switch 12 is a two-position push switch with switches SW1 and SW2. The SW2 is turned on after the SW1 is turned on. Half-pressing the emission switch 12 turns on the SW1, thereby generating a warm-up command signal S1 (see FIG. 5) for starting the warm-up of the X-ray tube 20. Fully pressing the emission switch 12 turns on the SW2, thereby generating an emission command signal S2.

Figure 5:
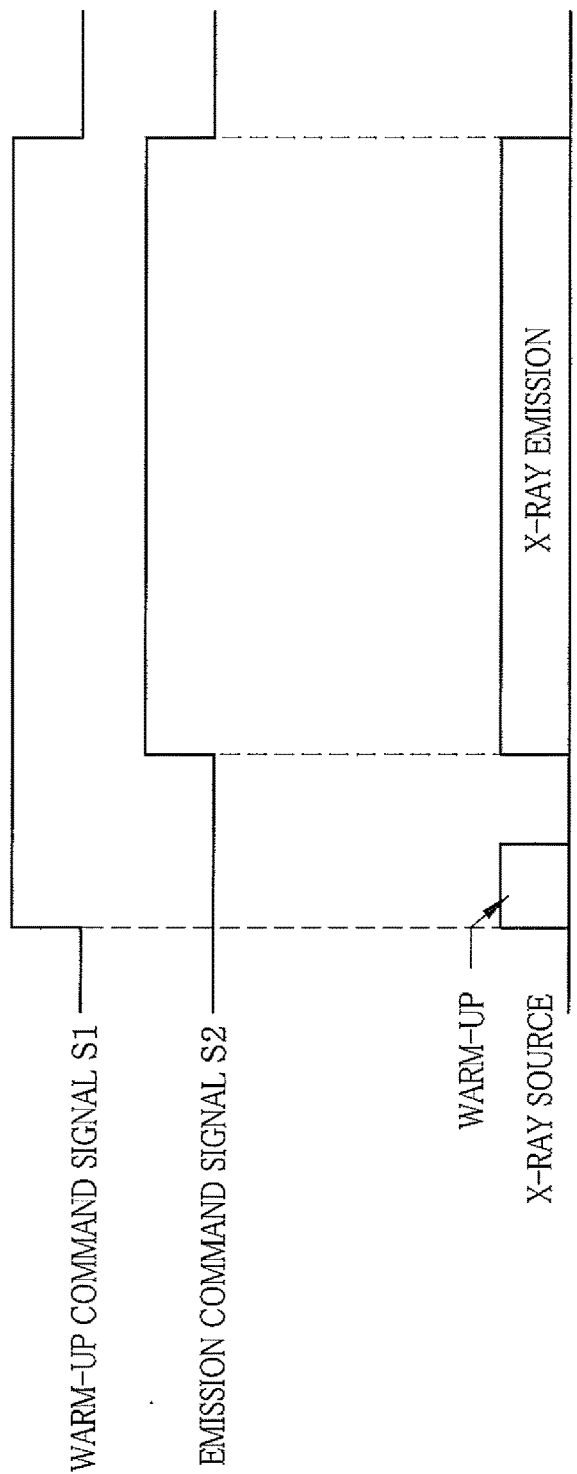
FIG. 5 is a timing chart illustrating operation of an emission switch and action of an X-ray source in an existing X-ray imaging system.

In the existing X-ray imaging system before the modifications, the emission switch 12 is directly connected to the switch I/F 31, so that the warm-up command signal S1 and the emission command signal S2 are inputted to the controller 26 of the source control device 11. As illustrated in FIG. 5, in response to the input of the warm-up command signal S1, the source control device 11 starts the warm-up of the X-ray source 10. The source control device 11 drives the X-ray source 10 to emit the X-rays while the emission command signal S2 is inputted. Namely, the emission execution signal from the signal relay device 15 is the same signal as the emission command signal S2 from the emission switch 12.

The electronic cassette 13 comprises a sensor panel 35 and a controller 36 that controls the operation of the sensor panel 35. The sensor panel 35 and the controller 36 are accommodated in a housing. The housing also accommodates a battery (secondary cell), a communication circuit, and the like. The battery supplies power to drive the electronic cassette 13. The communication circuit transmits data (e.g. an X-ray image) to the console 14. Note that data communication between the electronic cassette 13 and the console 14 may be wireless or wired. In the case of the wireless data communication, a communication unit, an antenna, and the like are also accommodated in the housing.

The size of the housing of the electronic cassette 13 is compliant with the international standards ISO (International Standards Organization) 4090:2001, as with those of the film cassette and the IP cassette 80, so that the electronic cassette 13 is detachably insertable to the holder 16a of the imaging stand 16 or the holder 17a of the imaging table 17. The electronic cassette 13 may be used singly. For example, the electronic cassette 13 may be placed on a bed on which the subject H lies down, or held by the subject H. Note that the size of the housing of the electronic cassette 13 may not be compliant with ISO 4090:2001.

The sensor panel 35 is of an indirect-conversion type, and comprises a TFT active matrix substrate and a scintillator (not shown), as is well known. The scintillator converts the X-rays into visible light. The scintillator (scintillator panel) may be attached to the TFT active matrix substrate, or the scintillator (scintillator layer) may be formed on the TFT active matrix substrate by vapor deposition. Alternatively, the sensor panel 35 may be of a direct-conversion type in which a conversion layer (amorphous selenium or the like) is formed in place of the scintillator on the TFT active matrix substrate. The conversion layer directly converts the X-rays into charge.

A plurality of pixels are arranged in a matrix in the TFT active matrix substrate. The pixels store the charges, the amounts of which correspond to the dose of the X-rays passed through the subject H. Each pixel comprises a photoelectric conversion unit and a TFT, as is well known. The photoelectric conversion unit generates a charge (electron-hole pair) in response to the incident visible light. The TFT is a switching element. The sensor panel 35 reads out a signal charge, which is stored in the photoelectric conversion unit of each pixel, to a signal processing circuit (not shown) through a signal line. The signal line is provided for each column of the pixels. The signal processing circuit converts the signal charges into a voltage signal and outputs it as an X-ray image signal. Note that the pixels may be arranged in a honeycomb pattern.

The scintillator and the TFT active matrix substrate are arranged in PSS (Penetration Side Sampling) configuration in which the scintillator and the TFT active matrix substrate are placed in this order from the X-ray incident side. Alternatively, the scintillator and the TFT active matrix substrate may be arranged in ISS (Irradiation Side sampling) configuration, in which the TFT active matrix substrate and the scintillator are placed in this order (in reverse order to that in the PSS system).

The controller 36 drives the TFTs through scanning lines, which correspond to the respective rows of the pixels, to allow the sensor panel 35 to perform a storage operation, a readout operation, or a reset operation. In the storage operation, the pixels store the signal charges in accordance with the X-ray dose. In the readout operation, the signal charges stored in the pixels are read out. In the reset operation, the dark charges occurred in the pixels are discharged. The controller 36 performs various types of image processing such as offset correction, sensitivity correction, and defect correction to the X-ray image data outputted from the sensor panel 35 through the readout operation.

The pixels include normal pixels (pixels for detecting an X-ray image) and measurement pixels (pixels for measuring a dose of the X-rays) 37. The normal pixels and the measurement pixels are placed in a mixed arrangement in two-dimensions in an image capture field 35a. The measurement pixels 37 are used as a dose measurement sensor that detects a delivered dose of the X-rays. The measurement pixels 37 are arranged (or distributed) uniformly without unevenness in the image capture field 35a. Actually, the size of each of the normal pixels and the measurement pixels 37 is small and there are a number of the normal pixels. In FIG. 2, only the measurement pixels 37 are schematically illustrated and the illustration of the normal pixels is omitted. A dose measurement signal from each of the measurement pixels 37 is transmitted to the signal processing circuit.

At the time of the X-ray imaging, the normal pixels are allowed to perform the storage operation, and store the signal charges in accordance with the delivered X-ray dose. On the other hand, the charge occurred in the measurement pixel 37 is read out as the dose measurement signal during the X-ray imaging. The measurement pixel 37 is a modified normal pixel. For example, the normal pixel is modified by short-circuiting the source electrode and the drain electrode of the TFT or by connecting the photoelectric converter directly to the signal line, without the TFT, to allow the charges to flow into the signal processing circuit irrespective of on and off of the TFT. A gate driver for measuring the dose may be provided separately from a gate driver for detecting the X-ray image, which provides the gate pulse to the TFT through the scanning line. The normal pixels driven by the gate driver for measuring the dose may be used as the measurement pixels. In this case, the configuration of the measurement pixel is the same as that of the normal pixel.

When the signal processing circuit and the sensor panel 35 are switched from a standby mode, in which the reset operation is repeated, to an imaging mode, in which the storage operation is started, sampling of the dose measurement signal from each measurement pixel 37 is started. For each sampling of the dose measurement signals, a determiner 38 selects the measurement pixels 37 contained in a radiation receiving area or dose measurement area which is set in accordance with the body part to be imaged. For each selected measurement pixel 37, a currently measured value obtained from the signal processing circuit is added to the integral value of the previously measured values to calculate the cumulative dose. The determiner 38 then calculates a representative value (the average value, the maximum value, the mode, the sum, or the like) based on the cumulative dose of each measurement pixel 37. The maximum value is the highest value among the cumulative doses of the measurement pixels 37. The mode is the cumulative dose that appears most frequently. The sum is the total value of the cumulative doses of the measurement pixels 37. The average value is obtained by dividing the sum by the number of the measurement pixels 37. The determiner 38 compares the representative value (e.g. the average value) with an emission stop threshold value (target dose).

Concurrently with the start of the sampling of the dose measurement signals, the determiner 38 starts outputting an emission enable signal S4 (see FIG. 4) to an emission signal I/F 39, and continues outputting the emission enable signal S4 while the average value is less than the emission stop threshold value. Upon determining that the average value exceeds the emission stop threshold value and the X-ray dose (radiation exposure dose) has reached the target dose during the X-ray imaging, the determiner 38 stops outputting the emission enable signal S4 to the emission signal I/F 39. Note that, in a case where the value of the dose measurement signal is obviously low due to an implant, the determiner 38 determines that the value is abnormal or an error. In this case, the output of the emission enable signal S4 may be stopped to suspend the X-ray emission.

A communication I/F 40 communicates with the console 14 via wire or wirelessly. Data (e.g. data of an X-ray image outputted from the sensor panel 35 or data of imaging conditions set through the console 14) is transmitted or received through the communication I/F 40.

The console 14 controls operation of the electronic cassette 13 in response to input operation of the operator through an input device 45 such as a keyboard or the like. The X-ray image transmitted from the electronic cassette 13 through the communication I/F 40 is displayed on a display 46 of the console 14. The data of the transmitted X-ray image is stored in a data storage device such as a storage device 47 or a memory in the console 14, or a data storage server or the like connected to the console 14 through a network.

The console 14 receives input of an examination order that includes information such as gender and age of the subject H, a body part to be imaged, a purpose of imaging, and the like, and displays the examination order on the display 46. The examination order may be received from an external system (e.g. Hospital Information System (HIS) or Radiology Information System (RIS)) for managing patient information and examination information related to examinations, or inputted manually by the operator. The examination order specifies the body part to be imaged (e.g. head, chest, abdomen, hand, finger, or the like) and the imaging direction (front, lateral, oblique, PA (the X-rays passing through the patient H from back to front), AP (the X-rays passing through the patient H from front to back), or the like). The operator checks the descriptions of the examination order on the display 46, and inputs the imaging conditions suitable for the examination order, with the use of the input device 45, to an operation screen displayed on the display 46.

The console 14 stores in advance the imaging conditions for each body part to be imaged. The imaging conditions include information such as the tube voltage, the tube current, the dose measurement area, and the emission stop threshold value. The emission stop threshold value is used for comparison with the integral value of the dose measurement signal to determine whether to stop the X-ray emission. The dose measurement area refers to an area in which the measurement pixels 37 used for the AEC are arranged. The dose measurement area corresponds to a region of interest, to which the maximum attention is paid at the diagnosis, of each body part to be imaged. The dose measurement area is set to the area from which the dose measurement signal is obtained stably. For example, in a case where the chest is to be imaged, left and right lung fields are set to be the dose measurement area. The information of the imaging conditions is stored in the storage device 47. The imaging conditions corresponding to the body part to be imaged, which is specified through the input device 45, are read out from the storage device 47, and transmitted to the electronic cassette 13 through the communication I/F 40. The imaging conditions, which include the tube voltage, the tube current, and the maximum irradiation time, used for the source control device 11 are manually set while the imaging conditions displayed on the display 46 of the console 14 are referred to.

The signal relay device 15 comprises three connection I/Fs: a first connection I/F 50, a second connection I/F 51, and a third connection I/F 52. The first connection I/F 50 is connected to the emission switch 12 through a cable. The second connection I/F 51 is connected to the emission signal I/F 39 of the electronic cassette 13 through a cable. The third connection I/F 52 is connected to the switch I/F 31 of the source control device 11 through a cable. The warm-up command signal S1 and the emission command signal S2 are inputted from the emission switch 12 to the first connection I/F 50. The second connection I/F 51 transmits an emission start request signal S3 (see FIG. 4) to the emission signal I/F 39 of the electronic cassette 13 and receives the emission enable signal S4 from the emission signal I/F 39. The third connection I/F 52 transmits the warm-up command signal S1 and an emission execution signal S6 to the switch I/F 31 of the source control device 11.

Figure 3:
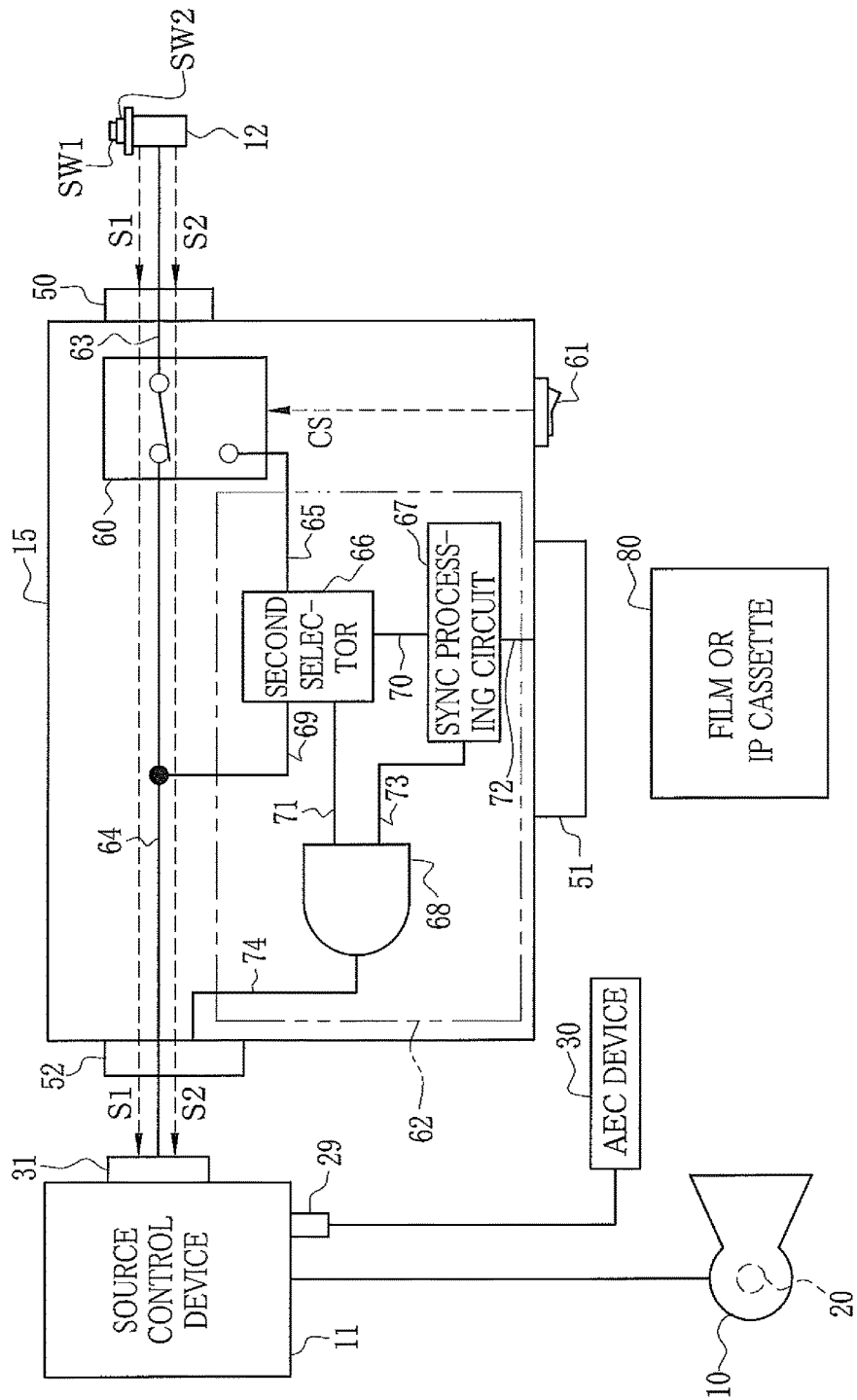
FIG. 3 is a block diagram of a signal relay device.
Figure 4:
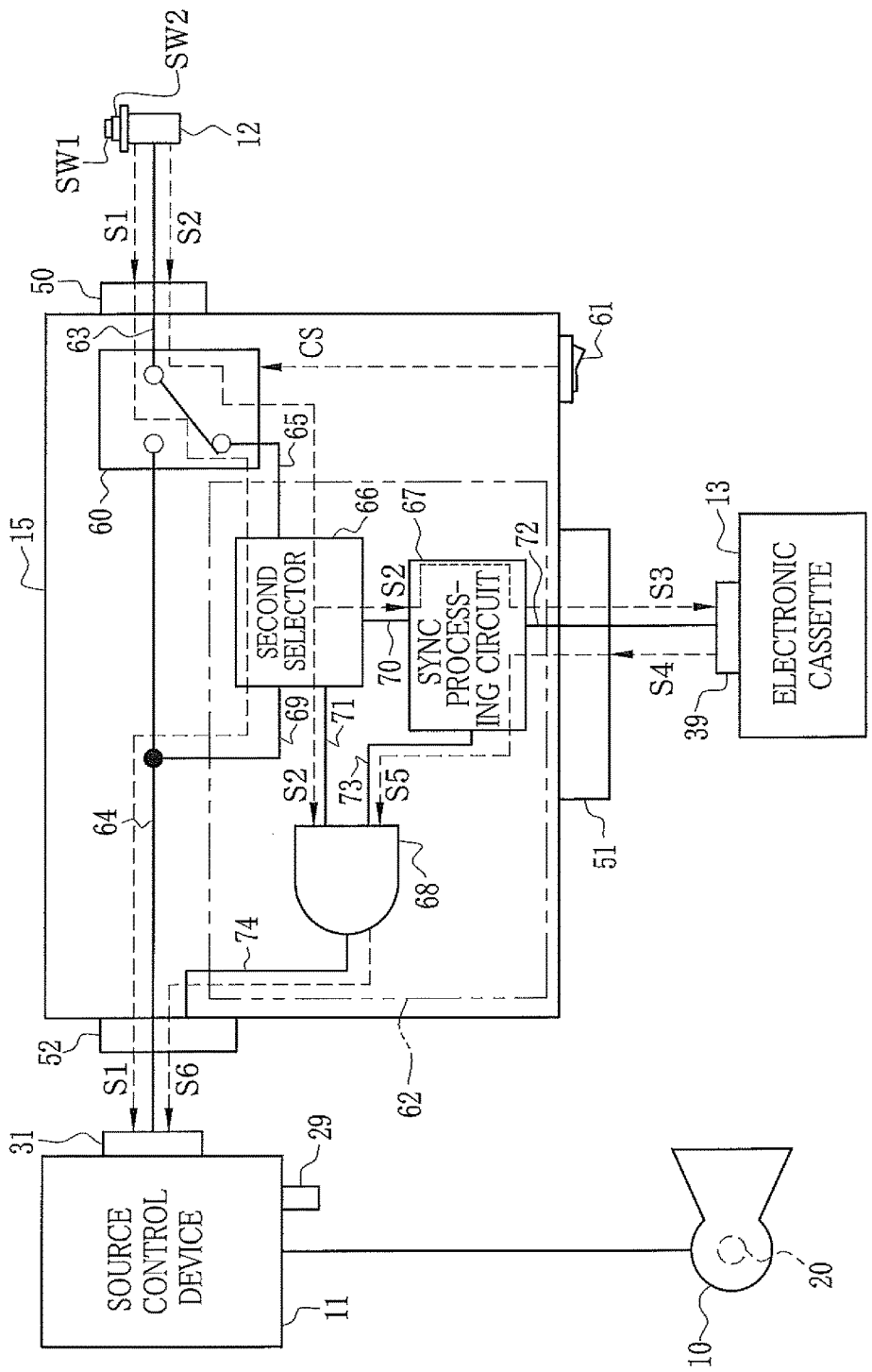
FIG. 4 is a block diagram illustrating a signal flow in a manner similar to FIG. 3.

In FIGS. 3 and 4, the signal relay device 15 comprises a first selector 60, a selector switch 61, and a signal processing unit 62. The selector switch 61, when operated externally, transmits a selection signal CS to the first selector 60, and thereby switches the signal relay device 15 to one of a through mode displayed in FIG. 3 and a conversion mode displayed in FIG. 4. In the through mode, the first selector 60 connects a signal line 63 to a signal line 64. In the conversion mode, the first selector 60 connects the signal line 63 to a signal line 65.

The through mode is chosen in the case where the existing X-ray imaging system with the film cassette or the IP cassette 80 is used. In the through mode, the emission command signal S2 from the first connection I/F 50 is transmitted through the signal lines 63 and 64, and outputted from the third connection I/F 52. The emission command signal S2 is inputted as the emission execution signal S6 to the source control device 11. As illustrated in FIG. 5, the source control device 11 drives the X-ray source 10 to emit the X-rays while the emission command signal S2 is inputted from the switch I/F 31. In the case where the AEC device 30 is used, the X-ray source 10 stops the X-ray emission in response to the input of the emission stop signal from the AEC device 30 to the source control device 11 through the AEC I/F 29, even while the emission command signal S2 is inputted.

The conversion mode is chosen in the case where the existing X-ray imaging system is modified into the electronic X-ray imaging system 2 using the electronic cassette 13. The emission command signal S2 is transmitted to the signal processing unit 62 by the first selector 60, for synchronization with the electronic cassette 13. The AEC function of the electronic cassette 13 is utilized.

The signal processing unit 62 comprises a second selector 66, a synchronization processing circuit (hereinafter referred to as sync processing circuit) 67, and an AND circuit 68. The second selector 66 transmits the warm-up command signal S1 or the emission command signal S2, which are inputted from the first selector 60 through the signal line 65, to signal line(s) 69, 70, or 71. The signal line 69 is connected to the signal line 64. The signal line 70 is connected to the sync processing circuit 67. The signal line 71 is connected to one of input terminals of the AND circuit 68.

In the conversion mode, in the case where the warm-up command signal S1 is inputted, the second selector 66 outputs the warm-up command signal S1 to the signal line 69. The warm-up command signal S1 is outputted from the third connection I/F 52 through the signal lines 69 and 64. In the case where the emission command signal S2 is inputted, the second selector 66 outputs the emission command signal S2 to each of the signal lines 70 and 71. The emission command signal S2 is inputted to the sync processing circuit 67 through the signal line 70. The emission command signal S2 is also inputted to one of the input terminals of the AND circuit 68 through the signal line 71.

The sync processing circuit 67 is connected to the second connection I/F 51 through a signal line 72. The sync processing circuit 67 is connected to the other of the input terminals of the AND circuit 68 through a signal line 73. In response to the input of the emission command signal S2 from the second selector 66 through the signal line 70, the sync processing circuit 67 outputs the emission start request signal S3 to the second connection I/F 51 through the signal line 72. The emission start request signal S3 is transmitted to ask whether to start the X-ray emission.

In response to the input of the emission enable signal S4 from the emission signal I/F 39 of the electronic cassette 13 through the second connection I/F 51 and the signal line 72, the sync processing circuit 67 outputs an ON signal S5 to the signal line 73, and stops outputting the ON signal S5 when the input of the emission enable signal S4 stops.

The AND circuit 68 is connected to the second selector 66, the sync processing circuit 67, and the third connection I/F 52 through the signal lines 71, 73, and 74, respectively. The AND circuit 68 calculates a logical product (or "AND") of the emission command signal S2 and the ON signal S5 inputted to the input terminals through the signal lines 71 and 73, respectively. The AND circuit 68 outputs the emission execution signal S6 from the output terminal in response to the input of both the emission command signal S2 and the ON signal S5 to the respective input terminals. In the case where the input of one of the emission command signal S2 and the ON signal S5 stops, the AND circuit 68 stops outputting the emission execution signal S6 from the output terminal. The emission execution signal S6 is inputted to the controller 26 of the source control device 11 through the signal line 74, the third connection I/F 52, a signal cable, and the switch I/F 31. The controller 26 drives the X-ray source 10 to emit the X-rays while the emission execution signal S6 is inputted.

Upon receiving the emission start request signal S3 through the emission signal I/F 39, the controller 36 of the electronic cassette 13 switches the operation of the sensor panel 35 from the reset operation to the storage operation, and thereby switches the sensor panel 35 from the standby mode to the imaging mode. The determiner 38 starts outputting the emission enable signal S4 to the emission signal I/F 39.

Figure 6:
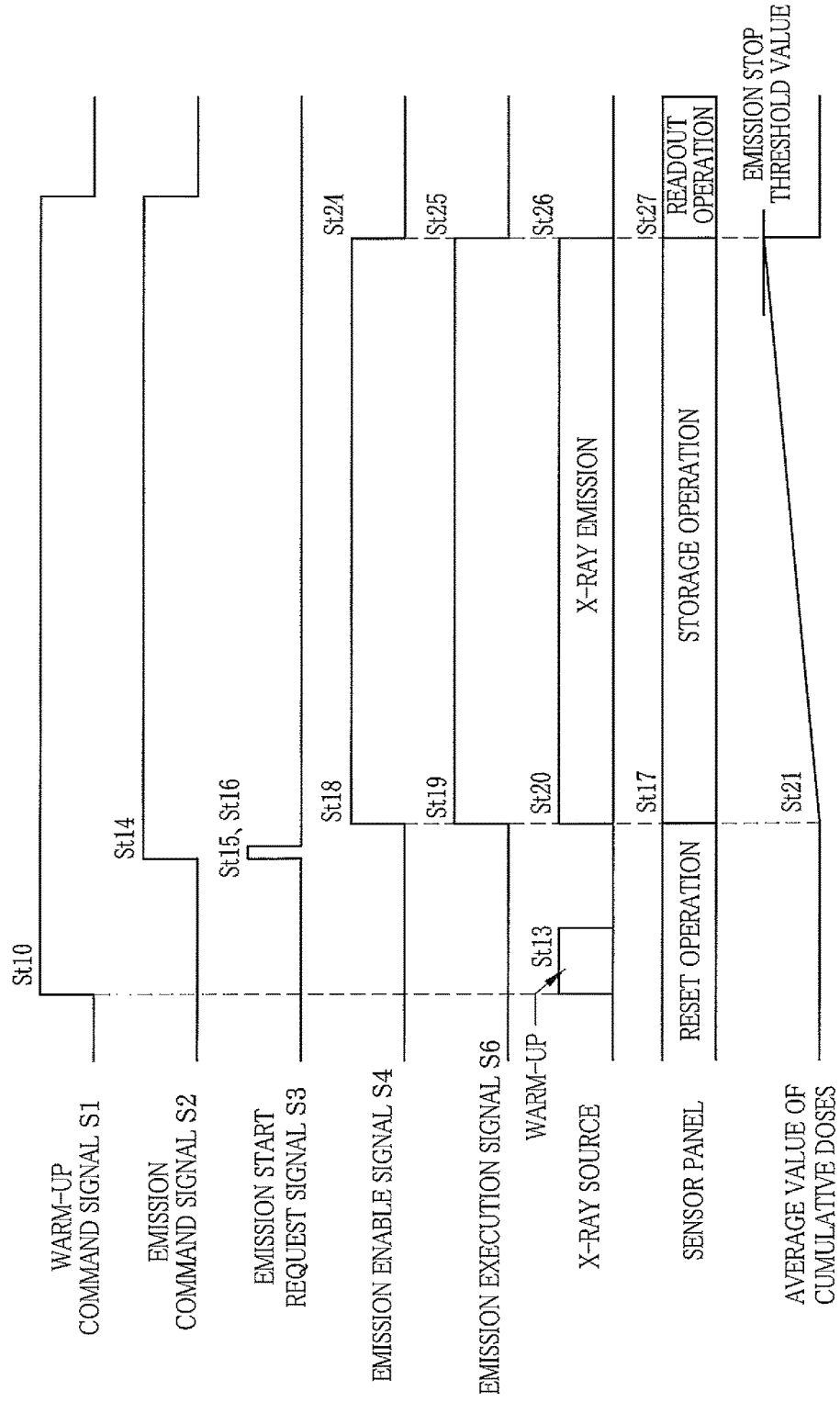
FIG. 6 is a timing chart for X-ray imaging with the electronic X-ray imaging system after the modification.
Figure 7:
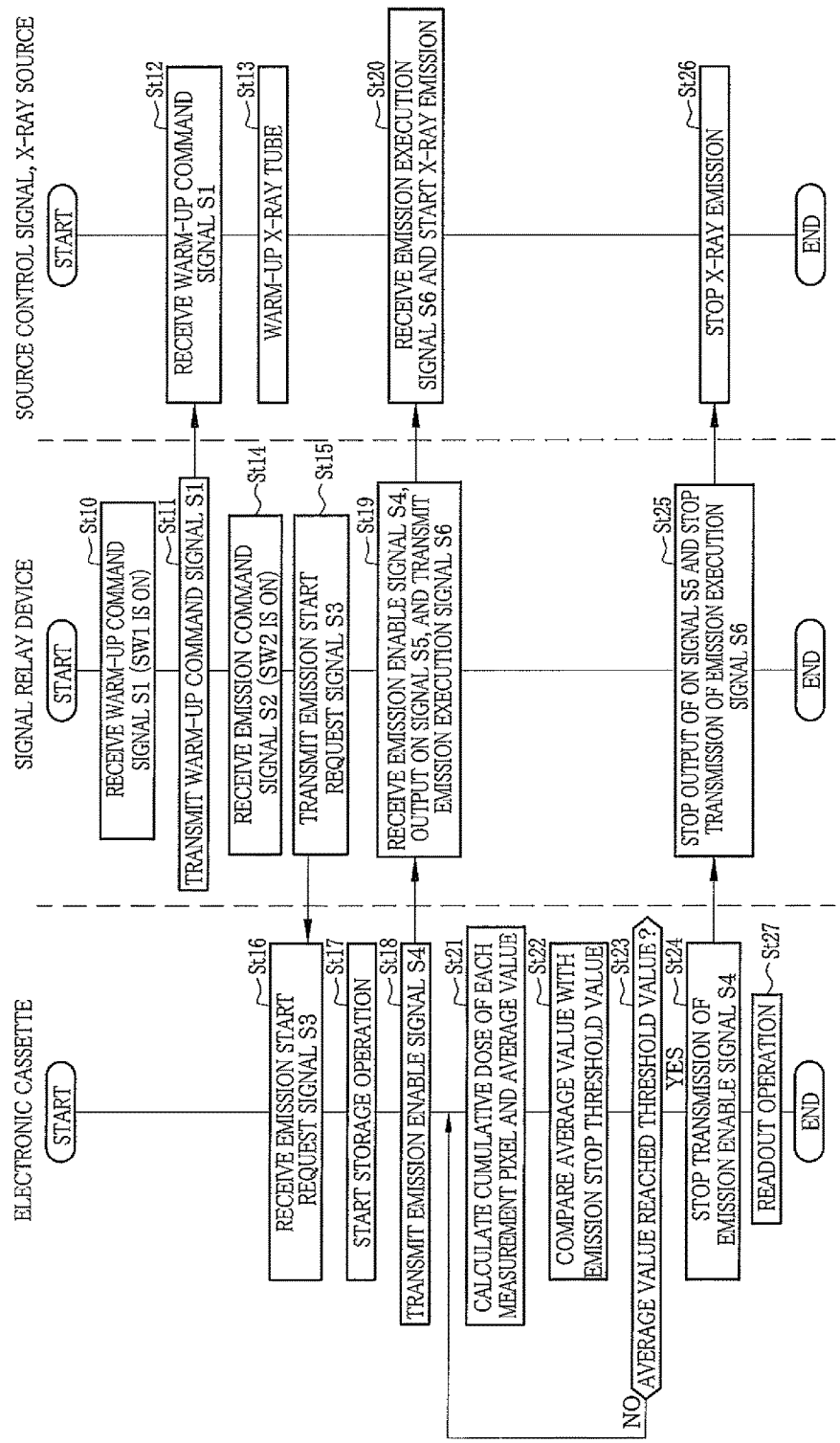
FIG. 7 is a flowchart illustrating a procedure of the X-ray imaging.

Next, referring to FIGS. 6 and 7, modifications to the existing X-ray generating apparatus 2a to achieve the electronic X-ray imaging system 2, which uses the electronic cassette 13, and an operation of the electronic X-ray imaging system 2 are described. To modify the existing X-ray imaging system which uses the X-ray film or the IP plate into the electronic X-ray imaging system 2, it is necessary to purchase or add the signal relay device 15, the console 14, and the electronic cassette 13, but the existing X-ray generating apparatus 2a is used without replacement. Note that the AEC device 30 is unnecessary in the electronic X-ray imaging system 2, so that the AEC device 30 is removed from the AEC I/F 29.

For the modifications, the emission switch 12 is connected to the first connection I/F 50 of the signal relay device 15. The second connection I/F 51 is connected to the emission signal I/F 39 through a signal cable. The third connection I/F 52 is connected to the switch I/F 31 through a signal cable. Then, the selector switch 61 of the signal relay device 15 is operated to choose the conversion mode. Thereby, as illustrated in FIG. 4, the first selector 60 connects the signal line 63 to the signal line 65, and thus the existing X-ray imaging system is modified into the electronic X-ray imaging system 2.

One of the imaging stand 16 and the imaging table 17 suitable for the body part to be imaged is chosen. The electronic cassette 13 is inserted into, for example, the imaging stand 16, after the subject H stands in front of the imaging stand 16. Then, the communication I/F 40 of the electronic cassette 13 is connected to the console 14. The height and the horizontal position of the holder 16a are adjusted to be suitable for the body part of the subject H to be imaged. The height, the horizontal position, the size of the irradiation field of the X-ray source 10 are adjusted to be suitable for the position and the size of the body part to be imaged.

The display 46 of the console 14 displays standard imaging conditions based on the examination order. The tube voltage, the tube current, the maximum irradiation time, an emission stop threshold value for stopping the X-ray emission, and the like are inputted through the input device 45 while the standard imaging conditions are referred to. The emission stop threshold value is transmitted to the electronic cassette 13.

After the preparation for imaging is completed, the electronic X-ray imaging system 2 is in the standby state for imaging. Each pixel of the sensor panel 35 performs the reset operation and discharges the stored dark charge at predetermined time intervals. In the stand-by state, half-pressing the emission switch 12 turns on the SW1, and thereby generates the warm-up command signal S1. The warm-up command signal S1 is transmitted to the signal relay device 15 (St10). In the signal relay device 15, the second selector 66 transmits the warm-up command signal S1 to the signal line 69. Then, the warm-up command signal S1 is outputted from the third connection I/F 52 through the signal line 64 (St11). Since the third connection I/F 52 is connected to the switch I/F 31, the warm-up command signal S1 is inputted to the source control device 11 (St12). Thereby, the high-voltage generator 25 starts supplying the power to the X-ray tube 20, and thus the warm-up of the X-ray tube 20 is started (St13).

After a lapse of the time necessary for the warm-up after the half-pressing, the emission switch 12 is fully pressed (the SW2 is turned on). Fully pressing the emission switch 12 generates the emission command signal S2. The emission command signal S2 is inputted to the signal relay device 15 (St14). The second selector 66 inputs the emission command signal S2 to the sync processing circuit 67 and the AND circuit 68 through the respective signal lines 70 and 71.

Upon the input of the emission command signal S2, the sync processing circuit 67 outputs the emission start request signal S3 (St15). The emission start request signal S3 is inputted to the electronic cassette 13 (St16). Thereby, the sensor panel 35 stops the reset operation and starts the storage operation (St17). At the same time, the output of the emission enable signal S4 to the emission signal I/F 39 is started (St18).

The emission enable signal S4 is inputted to the sync processing circuit 67 of the signal relay device 15, and converted into the ON signal S5. The ON signal S5 is transmitted to the AND circuit 68 through the signal line 73. Thereby, the logical product of the emission command signal S2 and the ON signal S5 becomes "1", and the AND circuit 68 outputs the emission execution signal S6 (St19). The emission execution signal S6 is inputted to the source control device 11 through the signal line 74, the third connection I/F 52, and the switch I/F 31. While the emission execution signal S6 is inputted, the controller 26 of the source control device 11 allows the high-voltage generator 25 to supply the high voltage to the X-ray source 10, allowing the X-ray tube 20 to emit the X-rays (St20).

An observation object (body part to be imaged) of the subject H is irradiated with the X-rays from the X-ray tube after the irradiation field of the X-rays is limited by the irradiation field limiter. The X-rays passed through the subject H are incident on the electronic cassette 13. In the electronic cassette 13, the scintillator converts the X-rays into the visible light. Each pixel in the sensor panel 35 converts the light into a charge.

The charge is stored in the normal pixel. On the other hand, the charge is discharged from the measurement pixel 37 to the signal processing circuit without being stored. The signal processing circuit converts the charge from each measurement pixel into a voltage. The signal processing circuit comprises integrators, each of which converts the charge into the voltage, as is well-known. After the digital conversion of the voltages from the integrators, the signal processing circuit transmits the digitally converted data as the dose measurement signal to the determiner 38. Each integrator is reset at relatively short intervals, so that the dose measurement is performed at predetermined intervals. The determiner 38 stores the total value of the previously measured values, and adds the currently measured value to the total value. Thus, the determiner 38 calculates the cumulative dose for each measurement pixel 37. The determiner 38 selects the measurement pixels 37 which are located within the dose measurement area, from all the measurement pixels, and calculates the representative value (e.g. the average value) based on the cumulative doses of the selected measurement pixels 37 (St21). Then, the determiner 38 compares the average value with the emission stop threshold value, for each measurement (St22).

When the average value reaches the emission stop threshold value during the X-ray imaging (YES in St23), the determiner 38 determines that the X-ray emission has been performed properly and stops the output of the emission enable signal S4 (St24). Thereby, the sync processing circuit 67 stops generating the ON signal S5, so that the logical product of the emission command signal S2 and the ON signal S5 becomes "0". Consequently, the AND circuit 68 stops the output of the emission execution signal S6 (St25). The input of the emission execution signal S6 to the source control device 11 also stops. The power supply from the high-voltage generator 25 to the X-ray tube 20 stops when the input of the emission execution signal S6 to the source control device 11 stops. This terminates the X-ray emission from the X-ray source 10 (St26).

After the termination of the X-ray emission, the determiner 38 switches the operation of the normal pixels of the sensor panel 35 from the storage operation to the readout operation (St27). Thereby, the charges stored in the normal pixels are converted by the signal processing circuit into voltages and then digitally converted, and temporarily stored as the X-ray image data in the memory. After the readout operation, the sensor panel 35 returns to the standby mode, in which the reset operation is performed, to be ready for the next X-ray imaging. The X-ray image data in the memory is subject to the various types of image processing performed by the controller 36 and then transmitted to the console 14 through the communication I/F 40. The console 14 displays the X-ray image on the display 46, to be used for diagnosis.

In the case of the X-ray imaging using the film cassette or the IP cassette 80, the operation mode is switched to the through mode by operating the selector switch 61. As illustrated in FIG. 3, in the through mode, the selection signal CS from the selector switch 61 is inputted to the first selector 60. The first selector 60 operates to connect the signal line 63 to the signal line 64. The AEC device 30 is set to the holder of the imaging stand or the imaging table, and then connected to the AEC I/F 29 of the source control device 11 as illustrated in FIG. 1. The film cassette or the IP cassette 80 is inserted into the holder of the imaging stand or imaging table chosen. Note that it is obviously unnecessary to connect the film cassette or the IP cassette 80 to the signal relay device 15 since the film cassette and the IP cassette 80 do not have electrical configurations.

After the preparation for imaging, the emission switch 12 is operated. Upon operating the emission switch 12, the warm-up command signal S1 and the emission command signal S2 just pass through the signal relay device 15 and then are inputted to the source control device 11. The X-ray tube 20 initiates the X-ray emission based on the emission command signal S2. During the X-ray imaging, the AEC device 30 measures the X-ray dose. Whether the measured dose has reached the target dose is determined. When the X-ray dose reaches the target dose, the AEC device 30 commands the source control device 11, through the AEC I/F 29, to terminate the X-ray emission. Thereby the X-ray emission from the X-ray tube 20 is terminated and the X-ray imaging is completed. In the case of the film cassette, the X-ray image is recorded on the X-ray film. In the case of the IP cassette 80, the X-ray image is recorded in the form of X-ray energy on the IP plate.

In the present invention, the signal relay device 15 has simple configuration composed of the selectors 60 and 66, the AND circuit 68, and the like. Therefore the modifications to achieve the electronic X-ray imaging system 2 is far more inexpensive than making modifications to the source control device 11 or replacing the source control device with the one used for the electronic cassette 13. The inexpensive cost prompts introducing the electronic X-ray imaging system 2.

The through mode, which is chosen through the operation of the selector switch 61, is provided to transmit the warm-up command signal S1 and the emission command signal S2 only to the source control device 11. This enables the use of the existing film cassette and the IP cassette 80 through a simple switching operation. Note that the through mode is unnecessary if the film cassette and the IP cassette 80 are not used after the modifications. In this case, it may be unnecessary to provide the first selector 60 and the selector switch 61.

The signal relay device 15 allows inputting the emission start request signal S3 to the electronic cassette 13 and outputting the emission enable signal S4 from the electronic cassette 13 through the single emission signal I/F 39. In other words, only the single signal cable for the AEC is connected to the electronic cassette 13, avoiding difficult handling of the electronic cassette 13 caused by a plurality of signal cables connected thereto.

In the above embodiments, the source control device 11 having the AEC I/F 29 is described by way of example. The electronic X-ray imaging system 2 according to the present invention may not use the AEC I/F 29. Thus, the present invention is also applicable to a source control device without the AEC I/F 29.

Generally, in the electronic X-ray imaging system 2, a thin plate-like grid may be disposed in front of the electronic cassette 13 to remove scattered X-rays, which occur when the X-rays pass through the subject H. In the grid, for example, long thin X-ray transmission layers and long thin X-ray absorption layers, each extending in a column direction of the pixels of the sensor panel 35, are arranged alternately in a row direction of the pixels of the sensor panel 35. The grid is placed between the subject H and the electronic cassette 13, facing the X-ray incident surface of the electronic cassette 13.

In a case where the movable grid is used, a bucky mechanism (grid moving mechanism) is provided to the imaging stand or imaging table. The bucky mechanism moves the grid during the X-ray imaging to reduce grid fringes, which are caused by the X-ray transmission layers and the X-ray absorption layers. An I/F for the bucky mechanism is provided to the source control device to synchronize the bucky mechanism with the start timing and the stop timing of the X-ray emission. The electronic cassette 13 is connected to the I/F for the bucky mechanism. The sensor panel 35 may be switched from the reset operation to the storage operation or the determiner 38 may control the start of outputting the emission enable signal S4 in response to the signal transmitted through the I/F for the bucky mechanism.

The communication between the emission signal I/F 39 of the electronic cassette 13 and the second connection I/F 51 of the signal relay device 15 is not limited to wired communication through the signal cable and may be wireless.

In the above embodiments, the high-level emission enable signal S4 is outputted continuously from the emission signal I/F 39 before the average value reaches the emission stop threshold value. Alternatively, the low-level emission enable signal may be outputted.

Figure 8:
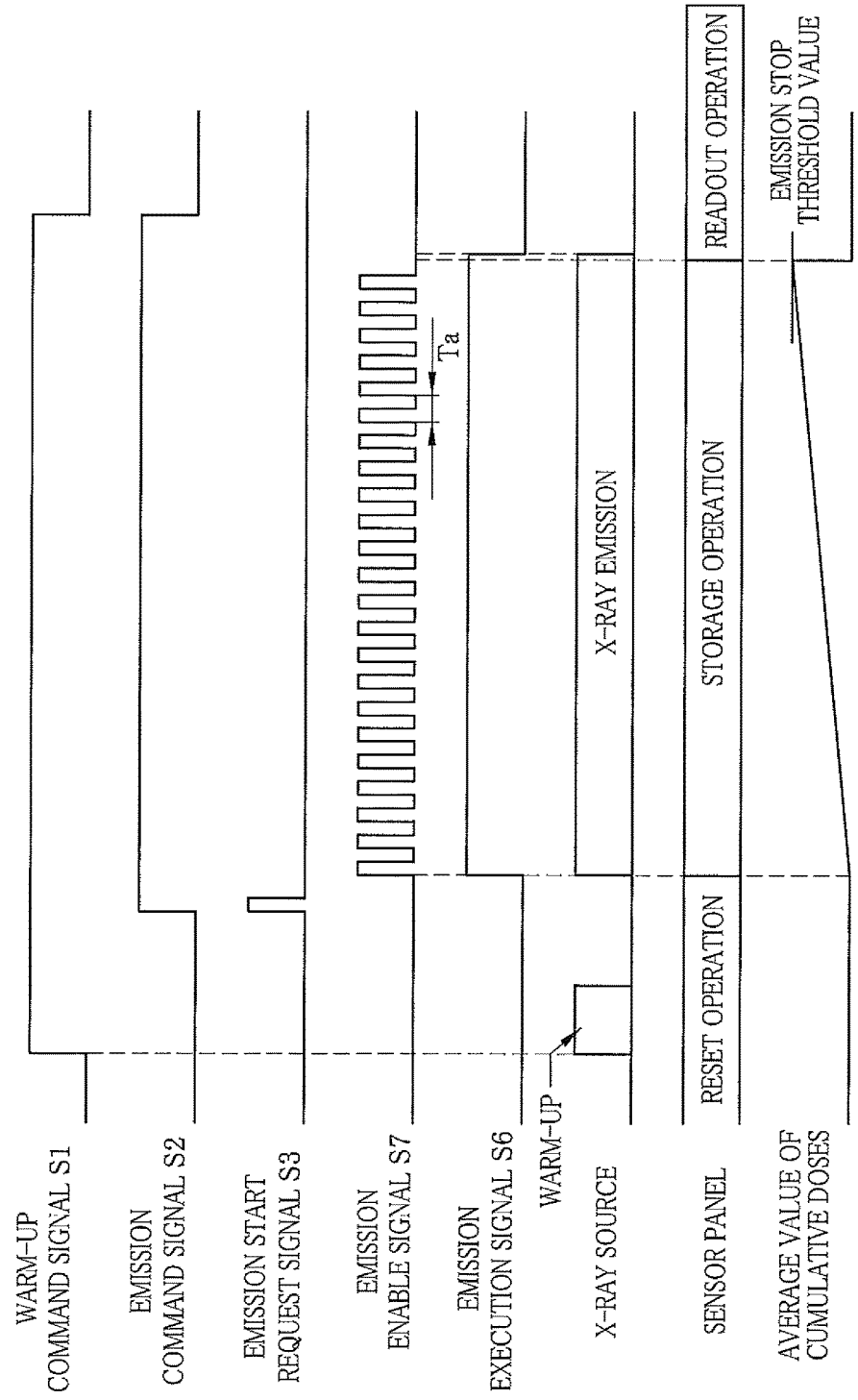
FIG. 8 is a timing chart for the X-ray imaging using an emission enable signal, being successive pulses.

As illustrated in FIG. 8, the emission enable signal S7 may be successive pulses, which rise and fall in predetermined time intervals Ta. The output of the emission enable signal S7 may be stopped when the cumulative dose of the X-rays reaches an appropriate value. As illustrated in FIG. 9, the emission enable signal S8 may be composed of separate single pulses (the emission start signal and the emission stop signal) each remaining at a high-level for a time period Tb.

In the case of the emission enable signal S7 in FIG. 8, the sync processing circuit 67 starts outputting the ON signal S5 when the emission enable signal S7 inputted to the second connection I/F 51 through the signal line 72 rises from the low level to the high level for the first time, in other words, when the first pulse of the emission enable signal S7 rises. The sync processing circuit 67 monitors a time period in which the emission enable signal S7 remains at the low level, and stops outputting the ON signal S5 when the time period becomes longer than a predetermined threshold value, for example, Ta/2 or Ta.

In the case of the emission enable signal S8 in FIG. 9, the sync processing circuit 67 starts outputting the ON signal S5 when the emission enable signal S8 inputted from the second connection I/F 51 through the signal line 72 rises for the first time, as with the case of the FIG. 8. The sync processing circuit 67 stops outputting the ON signal S5 when the emission enable signal S8 inputted from the second connection I/F 51 changes from the high level to the low level for the second time, in other words, when the emission enable signal S8 falls for the second time.

In either case, note that the output of the ON signal S5 is started in response to the detection of the first rise of the emission enable signal S7 or S8 inputted from the second connection I/F 51. Alternatively, the output of the ON signal S5 may be started in response to the detection of the first fall of the emission enable signal S7 or S8 inputted from the second connection I/F 51. In the case of FIG. 9, the output of the ON signal S5 may be stopped in response to the second rise of the emission enable signal S8 inputted from the second connection I/F 51. Alternatively, in the case of FIG. 9, a time period in which the emission enable signal S8 inputted from the second connection I/F 51 remains at the high level may be monitored. The output of the ON signal S5 is started when the time period reaches the predetermined threshold value Tb for the first time, and stopped when the time period reaches the threshold value Tb for the second time.

A switch for switching the operation (action) of the sync processing circuit 67 in accordance with the form of the signal output may be provided to allow the use the X-ray emission enable signals (or the emission start signal and the emission stop signal) having the signal waveforms illustrated in FIGS. 6, 8, and 9.

Not only the waveforms of the signals for enabling and stopping the X-ray emission but also the waveform of the emission command signal may be changed. In the above examples, in the waveform of the emission command signal S2, "1" is maintained while the emission switch 12 is fully pressed. Alternatively, a first single pulse may be outputted in response to fully pressing the emission switch 12, and a second single pulse may be outputted in response to releasing the full-pressing (releasing the emission switch 12). In this case, the signal processing unit retains the received first single pulse generated in response to fully pressing the emission switch 12. In response to the input of the emission enable signal S4 from the electronic cassette 13 while retaining the received first single pulse, the signal processing unit outputs the emission execution signal S6, which is equivalent to the single pulse, to the source control device 11.

Note that the emission command signal and the emission stop signal may be converted into form(s) other than the emission execution signal. Each of the emission command signal and the emission stop signal may take any form as long as it is receivable by the switch I/F. For example, the emission command signal may be directly outputted instead of outputting the emission execution signal from the signal relay device 15 to the source control device 11. The signal relay device may stop the output of the emission command signal upon the input of the emission stop signal from the electronic cassette to the signal relay device. In this case, the emission command signal also serves as the emission stop signal.

In the above embodiments, the output of the emission enable signal is stopped when the average value reaches the emission stop threshold value. Alternatively, the time estimated to be necessary for the average value to reach the emission stop threshold value may be calculated. The output of the emission enable signal is stopped when the irradiation time (exposure time) reaches the calculated estimated time.

Note that the dose may be measured by monitoring a current in a bias line, which supplies a bias voltage to each pixel in the sensor panel 35, because the current which is generated based on a charge in a pixel flows into the bias line. In this case, the measurement pixel is the pixel whose current flowing into the bias line is monitored. The measurement pixel also serves as the normal pixel. A leak current leaking or flowing from the pixel may be monitored to measure the dose. In this case, the measurement pixel is the pixel whose leak current is monitored. In the above embodiments, the measurement pixels are defective pixels in terms of detecting the X-ray image, but the measurement pixels are not the defective pixels in the case where the current in the bias line or the leak current is monitored, thereby improving the image quality of the X-ray image. Alternatively, a dose measurement sensor having configuration different from that of a pixel and an output path separately from that of the pixel may be provided in the image capture field.

In the above embodiments, the AEC function composed of the measurement pixels 37, the determiner 38, and the emission signal I/F 39 is incorporated in the electronic cassette 13, by way of example. Instead, the AEC function may be provided separately from the electronic cassette 13.

In the above embodiments, the console 14 and the electronic cassette 13 are provided separately, but the console 14 may not necessarily be an independent device. The console 14 may be equipped with the function of the electronic cassette 13. An exclusive image control device may be connected between the electronic cassette 13 and the console 14.

The X-ray image detection device is not limited to a portable type X-ray image detection device (e.g. the electronic cassette), and may be of a stationary type fixed to an imaging stand or imaging table. The present invention is applicable not only to the X-rays but to other types of radiation (e.g. gamma rays).

Various changes and modifications are possible in the present invention and may be understood to be within the present invention.

What is claimed is:

1. An electronic radiography system comprising:
   (A) a radiation generating apparatus comprising:
      a radiation source for emitting radiation to a subject;
      an emission switch for generating an emission command signal to command start of emission of the radiation; and
      a source control device having a switch I/F to which the emission command signal is inputted, the source control device allowing the radiation source to emit the radiation for radiography while the emission command signal is inputted;
   (B) an electronic radiographic image detection device comprising:
      a sensor panel for converting the radiation passed through the subject into an electric signal during the radiography and outputting a radiographic image of the subject;
      a dose measurement sensor for measuring a dose of the radiation during the radiography; and
      a controller for generating an emission enable signal, the emission enable signal determining a time period from a time when the emission is enabled in response to the emission command signal until a time for stopping the emission, the time for stopping the emission being determined by the controller through determining that a radiation exposure dose of the subject has reached a predetermined value based on measurement with the dose measurement sensor; and
   (C) a signal relay device comprising:
      a first connection I/F for receiving the emission command signal from the emission switch;
      a second connection I/F for transmitting the emission command signal to the electronic radiographic image detection device and receiving the emission enable signal from the electronic radiographic image detection device;
      a signal processing unit for generating an emission execution signal based on the emission command signal and the emission enable signal; and
      a third connection I/F for transmitting the emission execution signal to the switch I/F of the source control device,
   wherein the signal relay device is provided separately from the radiation generating apparatus.

2. The electronic radiography system according to claim 1, wherein normal pixels, which detect the radiographic image, and measurement pixels, being the dose measurement sensor, are placed in a mixed arrangement in two-dimensions in the sensor panel.

3. The electronic radiography system according to claim 2, wherein the electronic radiographic image detection device is an electronic cassette in which the sensor panel and the controller are accommodated in a portable housing.

4. The electronic radiography system according to claim 1, wherein the emission command signal is outputted continuously while the emission switch is operated.

5. The electronic radiography system according to claim 4, wherein the signal processing unit is configured to perform the steps of:
   (a) transmitting an emission start request signal to the electronic radiographic image detection device through the second connection I/F in response to input of the emission command signal, the emission start request signal asking whether to start the emission of the radiation;

(b) receiving the emission enable signal from the electronic radiographic image detection device through the second connection I/F;
(c) generating an ON signal in response to the emission enable signal, from the time when the emission is enabled until the time for stopping the emission; and
(d) generating the emission execution signal based on the emission command signal and the ON signal.

6. The electronic radiography system according to claim 5, wherein the signal processing unit comprises a synchronization processing unit for performing the steps (a) to (c) and an AND circuit for performing the step (d).

7. The electronic radiography system according to claim 5, wherein the emission enable signal has a waveform outputted continuously from the time when the emission is enabled until the time for stopping the emission.

8. The electronic radiography system according to claim 5, wherein the emission enable signal has a pulse waveform and is generated repeatedly at predetermined intervals from the time when the emission is enabled until the time for stopping the emission.

9. The electronic radiography system according to claim 5, wherein the emission enable signal has a pulse-like emission start signal generated at the time when the emission is enabled and a pulse-like emission stop signal generated at the time for stopping the emission.

10. The electronic radiography system according to claim 5, wherein the signal relay device has a conversion mode, which is chosen in a case where the electronic radiographic image detection device is used, and a through mode, which is chosen in a case where the electronic radiographic image detection device is not used; and
the signal processing unit is activated and the emission execution signal is generated in the conversion mode; and
the emission command signal inputted from the emission switch through the first connection I/F is inputted as the emission execution signal to the source control device through the third connection I/F in the through mode.

11. The electronic radiography system according to claim 10, wherein a radiographic image recording device using a radiation film or a radiographic image detection device using an IP plate is used in the through mode.

12. The electronic radiography system according to claim 11, wherein the emission switch generates a warm-up command signal, which commands warm-up of the radiation source, before outputting the emission command signal; and
the signal relay device outputs the warm-up command signal to the source control device through the third connection I/F.

13. A signal relay device used in an electronic radiography system comprising a radiation generating apparatus and an electronic radiographic image detection device, the radiation generating apparatus emitting radiation to a subject in response to input of an emission execution signal, the electronic radiographic image detection device detecting a radiographic image based on the radiation passed through the subject, the electronic radiographic image detection device generating an emission enable signal, the emission enable signal determining a time period from a time when emission of the radiation is enabled in response to an emission command signal until a time for stopping the emission, the time for stopping the emission being determined by determining that a radiation exposure dose of the subject has reached a predetermined value based on measurement with a dose measurement sensor, the signal relay device comprising:
a first connection I/F for receiving the emission command signal from an emission switch, being a component of the radiation generating apparatus;
a second connection I/F for transmitting the emission command signal to the electronic radiographic image detection device and receiving the emission enable signal from the electronic radiographic image detection device;
a signal processing unit for generating the emission execution signal based on the emission command signal and the emission enable signal; and
a third connection I/F for transmitting the emission execution signal to the source control device,
wherein the signal relay device is provided separately from the radiation generating apparatus.

14. The signal relay device according to claim 13, further configured to perform the steps of:
(a) transmitting an emission start request signal to the electronic radiographic image detection device through the second connection I/F in response to input of the emission command signal, the emission start request signal asking whether to start the emission of the radiation;
(b) receiving the emission enable signal from the electronic radiographic image detection device through the second connection I/F;
(c) generating an ON signal in response to the emission enable signal, the ON signal being generated from the time when the emission is enabled until the time for stopping the emission; and
(d) generating the emission execution signal based on the emission command signal and the ON signal.

15. The signal relay device according to claim 14, wherein the signal processing unit comprises a synchronization processing unit for performing the steps (a) to (c) and an AND circuit for performing the step (d).

16. The signal relay device according to claim 14, wherein the signal relay device has a conversion mode, which is chosen in a case where the electronic radiographic image detection device is used, and a through mode, which is chosen in a case where the electronic radiographic image detection device is not used; and
the signal processing unit is activated and the emission execution signal is generated in the conversion mode; and
the emission command signal inputted from the first connection I/F is inputted as the emission execution signal to the source control device through the third connection I/F in the through mode.

17. The electronic radiography system according to claim 1, further comprising:
(D) a console for controlling an operation of the electronic radiographic image detection device, the console being provided separately from the signal relay device.

* * * * *